(12) United States Patent
Kobayashi

(10) Patent No.: US 11,730,435 B2
(45) Date of Patent: Aug. 22, 2023

(54) MAMMOGRAPHY APPARATUS

(71) Applicant: Canon Medical Systems Corporation, Otawara (JP)

(72) Inventor: Yoshimasa Kobayashi, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 40 days.

(21) Appl. No.: 16/952,260

(22) Filed: Nov. 19, 2020

(65) Prior Publication Data

US 2021/0153831 A1    May 27, 2021

(30) Foreign Application Priority Data

Nov. 22, 2019   (JP) .................................. 2019-211331

(51) Int. Cl.
*A61B 6/00* (2006.01)
*A61B 6/04* (2006.01)

(52) U.S. Cl.
CPC ............ *A61B 6/502* (2013.01); *A61B 6/0414* (2013.01); *A61B 6/0435* (2013.01); *A61B 2562/0247* (2013.01)

(58) Field of Classification Search
CPC .......... A61B 2562/0247; A61B 6/0414; A61B 6/0435; A61B 6/06; A61B 6/4441; A61B 6/502; A61B 6/54
See application file for complete search history.

(56) References Cited

U.S. PATENT DOCUMENTS

| | | | | |
|---|---|---|---|---|
| 7,443,950 | B2 * | 10/2008 | Sendai | A61B 6/0414 378/62 |
| 11,234,660 | B2 * | 2/2022 | Talgorn | A61B 6/04 |
| 2007/0036265 | A1 * | 2/2007 | Jing | A61B 6/4429 378/37 |
| 2007/0274438 | A1 * | 11/2007 | Hyvarinen | A61B 6/502 378/37 |
| 2008/0080668 | A1 * | 4/2008 | Kashiwagi | A61B 6/54 378/37 |

(Continued)

FOREIGN PATENT DOCUMENTS

| | | |
|---|---|---|
| JP | 2007-125367 A | 5/2007 |
| JP | 2008-86451 | 4/2008 |

(Continued)

OTHER PUBLICATIONS

Japanese Office Action dated Apr. 25, 2023 in Japanese Application No. 2019-211331, 3 pgs.

*Primary Examiner* — Dani Fox
*Assistant Examiner* — Soorena Kefayati
(74) *Attorney, Agent, or Firm* — Oblon, McClelland, Maier & Neustadt, L.L.P.

(57) ABSTRACT

According to one embodiment, a mammography apparatus includes: a breast placement stage on which a breast is placed; a compression plate that compresses the breast placed on the breast placement stage; a supporting arm that supports the breast placement stage in such a manner that the stage can be tilted; and processing circuitry that controls driving of the compression plate in such a manner that the breast placed on the breast placement stage tilted by the supporting arm is supported from below and compressed.

5 Claims, 14 Drawing Sheets

(56) References Cited

U.S. PATENT DOCUMENTS

| | | | | |
|---|---|---|---|---|
| 2008/0181361 | A1* | 7/2008 | Eldered | A61B 6/502 378/37 |
| 2008/0240346 | A1* | 10/2008 | Kashiwagi | A61B 6/502 378/108 |
| 2009/0304159 | A1* | 12/2009 | Meer | A61B 6/502 378/208 |
| 2009/0323893 | A1* | 12/2009 | Hanke | A61B 6/4007 382/131 |
| 2012/0224664 | A1* | 9/2012 | Maack | A61B 6/502 378/7 |
| 2012/0277625 | A1* | 11/2012 | Nakayama | A61B 6/0414 250/393 |
| 2013/0131509 | A1* | 5/2013 | Rafaeli | A61B 6/4258 600/436 |
| 2013/0163716 | A1* | 6/2013 | Okada | A61B 6/502 378/19 |
| 2014/0135623 | A1* | 5/2014 | Manak | A61B 8/5261 600/427 |
| 2014/0226786 | A1* | 8/2014 | Goossen | A61B 6/0414 378/37 |
| 2015/0265186 | A1* | 9/2015 | Kuwabara | A61B 5/708 378/37 |
| 2016/0183889 | A1* | 6/2016 | Matsuura | A61B 6/54 378/37 |
| 2016/0206229 | A1* | 7/2016 | Arai | A61B 5/1075 |
| 2016/0249868 | A1* | 9/2016 | Nakayama | A61B 6/4233 378/4 |
| 2019/0239841 | A1* | 8/2019 | Han | A61B 6/06 |

FOREIGN PATENT DOCUMENTS

| | | |
|---|---|---|
| JP | WO 2015/045484 A1 | 4/2015 |
| JP | 2015-177884 A | 10/2015 |
| JP | 2016-123613 A | 7/2016 |

* cited by examiner

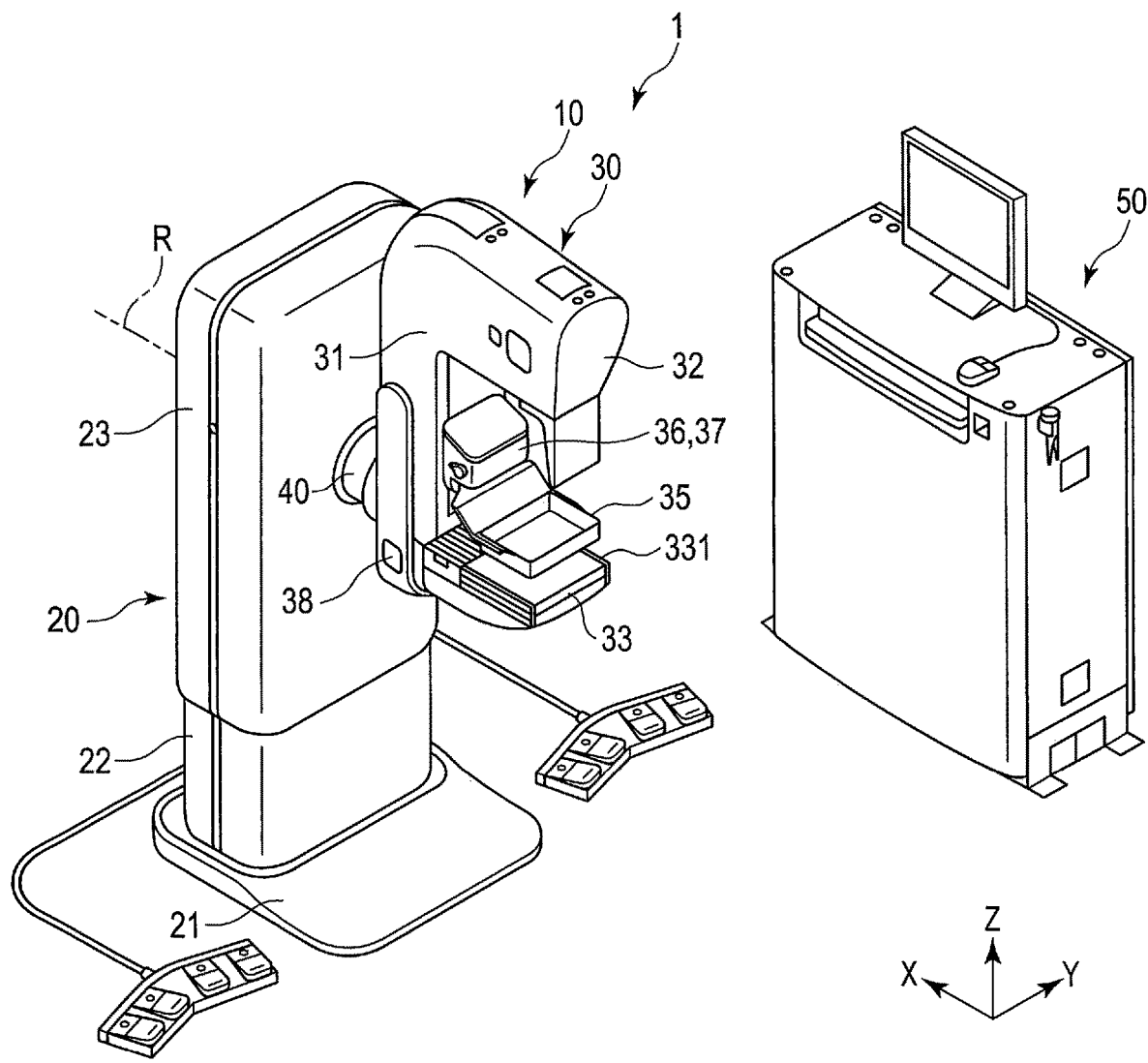
F I G. 2

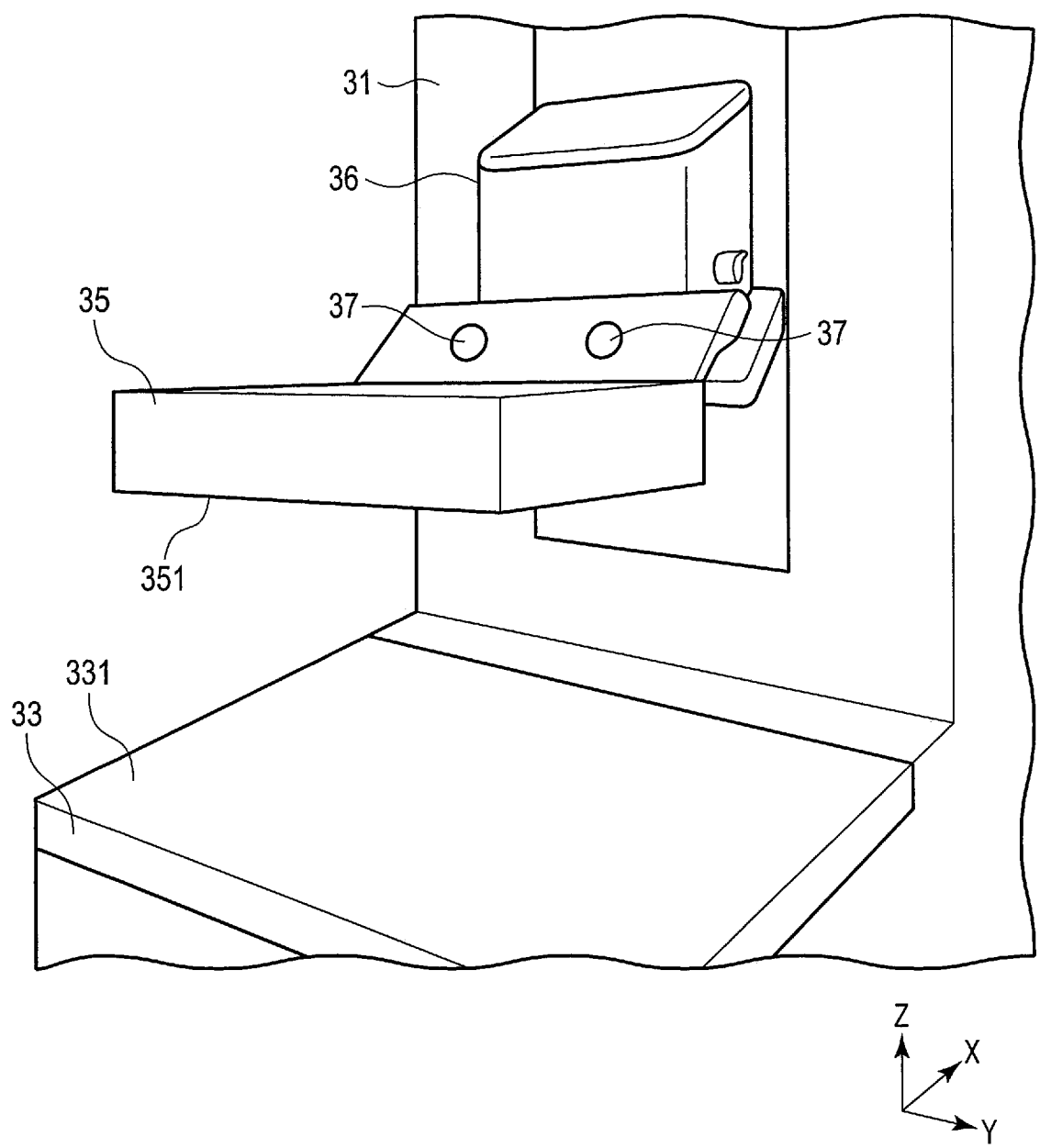
F I G. 3

| Imaging angle $\alpha$(deg) | Target tilt angle $\theta X$(deg) |
|---|---|
| 0 | 0 |
| 10 | 0 |
| 20 | $\theta 1$ |
| 30 | $\theta 2$ |
| 40 | $\theta 3$ |
| 50 | $\theta 4$ |
| 60 | $\theta 5$ |
| 70 | $\theta 6$ |
| 80 | $\theta 7$ |
| 90 | $\theta 8$ |

F I G. 4

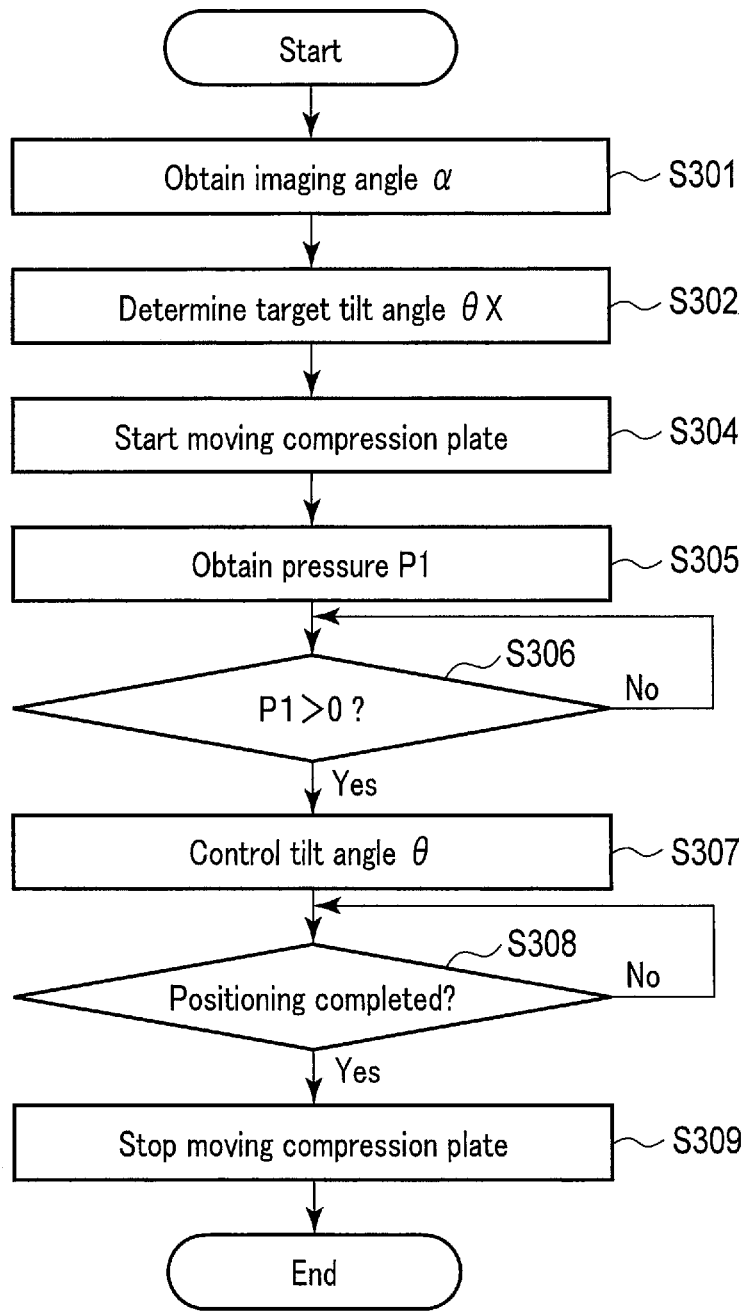
F I G. 15

MAMMOGRAPHY APPARATUS

CROSS-REFERENCE TO RELATED APPLICATIONS

This application is based upon and claims the benefit of priority from the prior Japanese Patent Application No. 2019-211331, filed Nov. 22, 2019, the entire contents of which are incorporated herein by reference.

FIELD

Embodiments described herein relate generally to a mammography apparatus.

BACKGROUND

A mammography apparatus is an X-ray imaging apparatus used exclusively for breasts, which specializes in compressing a breast placed on an imaging stage, flattening out the mammary gland, and collecting single-direction two-dimensional images of the breast. Since a mammary gland in a breast has a three-dimensionally branched structure that leads to lobules, superimposition of mammary gland components is often observed, and this interferes with accurate examination of a breast. For this reason, a breast is compressed and flattened out, so that superimposition of the mammary gland components can be eliminated and X-ray imaging can be performed with a smaller dose of X-rays.

In image diagnosis using a mammography apparatus, in some cases, not only a CC (craniocaudal) view but also an MLO (mediolateral oblique) view are obtained. In the MLO-view imaging, when positioning is carried out or immediately after positioning is completed, a breast may deviate to a position lower than a correct position because of its own weight. As a result, X-ray imaging is not performed at a correct position, and appropriate images cannot be obtained. When imaging is performed on a large breast, this problem becomes more pronounced. In order to prevent deviation of a breast from the correct position, a radiologic technologist needs to lift up and strongly compress a breast by hand to position the breast correctly.

To position a large breast, a radiologic technologist must even out the breast by force, and then apply force by hand to the flattened breast so that the breast does not return to its original shape and compress, while also retracting their hands. Manually compressing breasts is exhausting for radiologic technologists. It is especially difficult at an event such as a group health checkup where more than 30 people undergo X-ray imaging in one day.

BRIEF DESCRIPTION OF THE DRAWINGS

FIG. 2 is a diagram illustrating an outer appearance of the mammography apparatus according to the first embodiment.

FIG. 3 is a diagram showing a configuration example of a compression plate, a compression plate moving mechanism, and a compression plate tilting mechanism according to the first embodiment.

FIG. 4 is a diagram showing an example of a correspondence table of the relationship between an imaging angle and a target value of a tilt angle according to the first embodiment.

FIG. 15 is a flowchart illustrating an example of procedures of a positioning process performed by the mammography apparatus according to the third embodiment.

DETAILED DESCRIPTION

According to one embodiment, a mammography apparatus includes: a breast placement stage on which a breast is placed; a compression plate that compresses the breast placed on the breast placement stage; a supporting arm that supports the breast placement stage in such a manner that the stage can be tilted; and processing circuitry that controls driving of the compression plate in such a manner that the breast placed on the breast placement stage tilted by the supporting arm is supported from below and compressed.

An object is to suppress deviation of a breast from a correct position due to its own weight when breast positioning is performed.

Hereinafter, the embodiments of the X-ray diagnosis apparatus will be explained in detail with reference to the accompanying drawings. In the description hereinafter, structural elements having substantially the same functions and configurations will be denoted by the same reference symbols, and a duplicate description of such elements will be given only where necessary. In the following descriptions, a "mammography apparatus" may be called an "X-ray diagnosis apparatus" or "breast X-ray imaging apparatus".

First Embodiment

Figure 1:
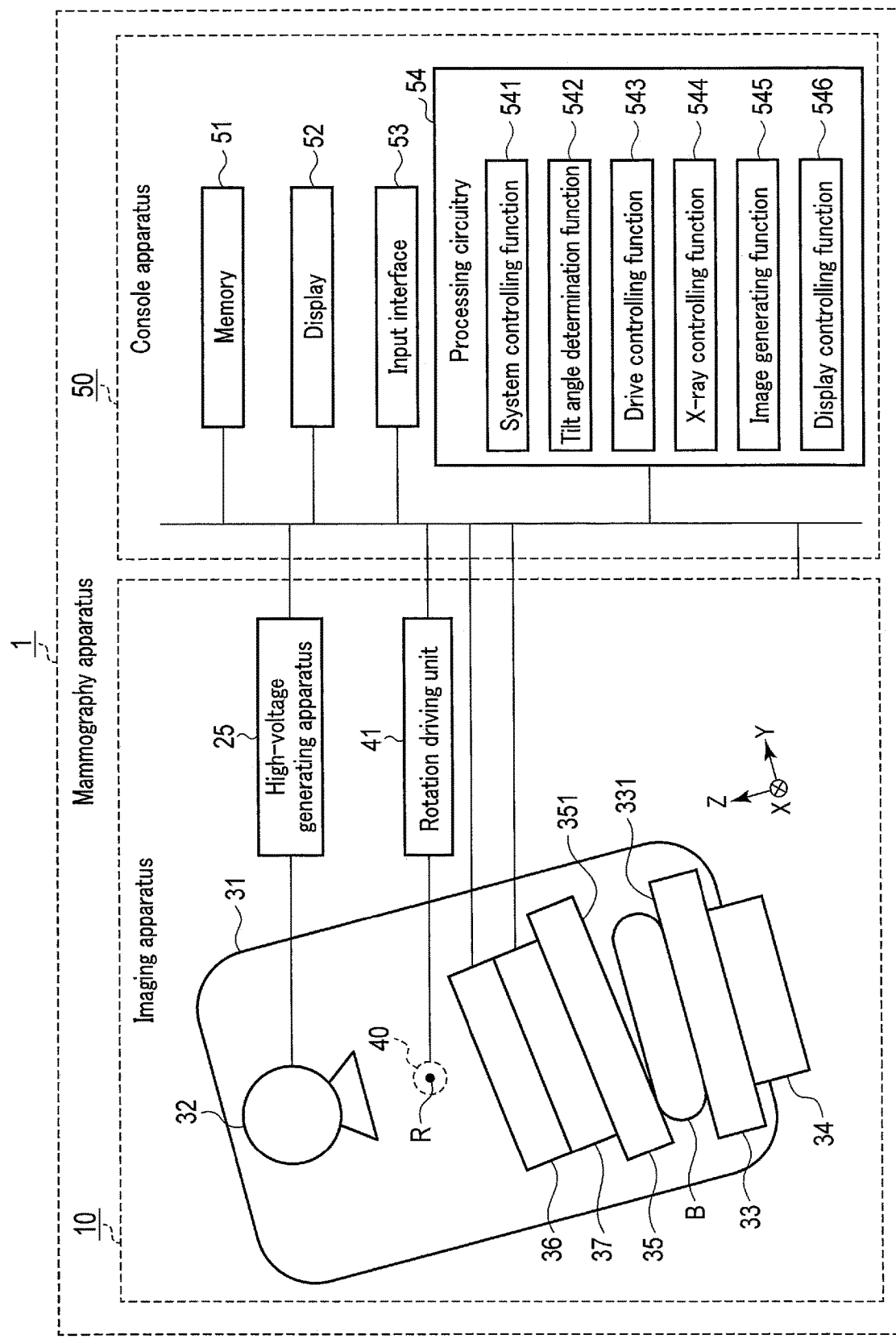
FIG. 1 is a diagram illustrating a configuration of a mammography apparatus according to a first embodiment.

FIG. 1 is a diagram illustrating a configuration of a mammography apparatus 1 according to the first embodiment. FIG. 2 is a diagram showing an outer appearance of the mammography apparatus 1. As shown in FIGS. 1 and 2, the mammography apparatus 1 includes an imaging apparatus 10 and a console apparatus 50. The imaging apparatus 10 includes a supporting unit 20, an imaging unit 30, and a supporting axis 40.

The supporting unit 20 is placed on a floor surface or a wall surface of an examination room, and supports the imaging unit 30. The supporting unit 20 supports the imaging unit 30 via the supporting axis 40. The supporting axis 40 has a center axis R. The supporting axis 40 rotates about the center axis R with respect to the supporting unit 20. The center axis R is a rotation axis of the imaging unit 30.

On the inside of the supporting unit 20, the rotation driving unit 41 for rotating the supporting axis 40 is accommodated. The rotation driving unit 41 is a rotation mechanism and/or a driving unit for rotating the supporting axis 40, and is connected to the supporting axis 40. The rotation driving unit 41 is realized by, for example, a gear, a stepping motor, a belt conveyor, or a lead screw, etc. The rotation driving unit 41 causes the supporting axis 40 to rotate around the center axis R with respect to the supporting unit 20, in accordance with rotation angle information of the supporting axis 40. Then, the imaging unit 30 connected to the supporting unit 20 via the supporting axis 40 is rotated around the center axis R by the rotation driving unit 41. When the imaging unit 30 is rotated around the center axis R, imaging in a craniocaudal (CC) direction (hereinafter, "CC-view imaging"), and imaging in a mediolateral-oblique (MLO) direction (hereinafter "MLO-view imaging"), etc. can be performed.

The supporting unit 20 has a base 21, a first support post 22, and a second support post 23. The base 21 is placed on a floor surface or a wall surface of an examination room. The first support post 22 is supported by the base 21, and supports the second support post 23. On the inside of the first support post 22 and the second support post 23, a vertical movement mechanism and a driving unit for raising and lowering the second support post 23 with respect to the first support post 22 are accommodated. When imaging is performed, the height of the second support post 23 is adjusted by the vertical movement mechanism in accordance with a patient's height. The supporting unit 20 may be called a "stand".

A high-voltage generating apparatus 25 is accommodated in the supporting unit 20. The high-voltage generating apparatus 25 generates a high voltage to be applied between an anode and a cathode, and outputs the high voltage to an X-ray tube, so that thermoelectrons generated from the cathode of the X-ray tube are accelerated. The high-voltage generating apparatus 25 may be accommodated in the console apparatus 50. The supporting unit 20 is an example of a support stage.

The imaging unit 30 includes a supporting arm 31, an X-ray generator 32, a breast placement stage 33, an X-ray detector 34, a compression plate 35, a compression plate moving mechanism 36, a compression plate tilting mechanism 37, and an operation panel 38.

The supporting arm 31 supports the X-ray generator 32, the breast placement stage 33, the X-ray detector 34, the compression plate 35, the compression plate moving mechanism 36, the compression plate tilting mechanism 37, and the operation panel 38. The supporting arm 31 is connected to the supporting axis 40. When the supporting axis 40 rotates, the supporting arm 31 rotates around the center axis R with respect to the supporting unit 20, together with the X-ray generator 32, the breast placement stage 33, the X-ray detector 34, the compression plate 35, the compression plate moving mechanism 36, the compression plate tilting mechanism 37, and the operation panel 38. The supporting arm 31 supports the breast placement stage 33 in such a manner that the breast placement stage 33 can be tilted. The supporting arm 31 supports the X-ray generator 32, the breast placement stage 33, the X-ray detector 34, and the compression plate 35, with the placement surface 331 (described later) being tilted with respect to the horizontal plane. The supporting arm 31 may be called a "C-arm".

The X-ray generator 32 includes an X-ray tube that irradiates a subject with X-rays, and an X-ray diaphragm. The X-ray generator 32 may be called an "X-ray tube apparatus".

The X-ray tube is a vacuum tube that generates X-rays. The X-ray tube has a tube bulb, a filament (cathode) provided on the tube bulb, and a tungsten anode. The X-ray tube accelerates the thermoelectrons released from the filament by the high voltage. The X-ray tube generates X-rays by making the accelerated electrons collide with the tungsten anode.

The X-ray diaphragm is located between the X-ray tube and the breast placement stage 33. The X-ray diaphragm is constituted by a metal plate, such as a lead plate. The X-ray diaphragm shields X-rays outside of its opening area so as to narrow the irradiation range of X-rays generated by the X-ray tube (hereinafter, "X-ray irradiation range") to a subject's breast. The X-ray diaphragm adjusts the area from which X-rays are shielded into a desired size so as to adjust the size of the X-ray irradiation range. The X-ray diaphragm is driven by a driving apparatus (not shown) in accordance with the size of the X-ray irradiation range that has been input by the operator with the input interface 53.

The breast placement stage 33 is arranged so as to face the X-ray generator 32. A patient's breast is placed on the breast placement stage 33. The breast placement stage 33 supports the patient's breast placed thereon. The breast placement stage 33 may be called an "imaging stage". On the inside of the supporting arm 31, a driving unit for moving the breast placement stage 33 is accommodated. The driving unit is realized by, for example, a gear, a stepping motor, a belt conveyor, or a lead screw, etc., and is connected to the breast placement stage 33. The driving unit moves the breast placement stage 33 with respect to the supporting arm 31 in accordance with the location information of the breast placement stage 33. A patient is an example of the subject.

The breast placement stage 33 has a placement surface 331. The placement surface 331 faces the X-ray generator 32. The placement surface 331 is a flat surface on which a patient's breast is placed. The placement surface 331 may be called an "imaging surface".

The X-ray detector 34 is accommodated in the breast placement stage 33. The X-ray detector 34 is arranged to oppose the X-ray generator 32. The X-ray detector 34 detects X-rays that have been emitted from the X-ray tube and have passed through the breast B placed on the breast placement stage 33. As the X-ray detector 34, both an X-ray detector capable of directly converting X-rays into electric charge and an X-ray detector capable of converting X-rays into light and then into electric charge can be adopted, and the former detector will be described hereinafter as an example; however, the latter detector can also be adopted. The X-ray detector 34 has a flat panel detector (FPD) that converts X-rays passed through a breast into electric charge and accumulates the electric charge, and a gate driver that generates a drive pulse for reading the electric charge accumulated in this FPD. The FPD is comprised of micro-detection elements, which are two-dimensionally arranged in a row direction and a line direction. Each of the detection elements has a photoelectric film that senses X-rays and generates electric charge in accordance with an amount of incident X-rays, an electric charge accumulating capacitor that accumulates electric charge generated on the photoelectric film, and a TFT (thin-film transistor) that outputs the electric charge accumulated on the electric charge accumulating capacitance at a predetermined timing. The accumulated electric charge is sequentially read by a drive pulse supplied by the gate driver. For the X-ray detector 34, a film cartridge or a CR cartridge may be adopted.

Herein, the direction along the center axis R is defined as an X direction, and the direction passing through the center of the detection surface of the X-ray detector 34 and a focal point of the X-ray tube (hereinafter, "imaging direction") is defined as a Z direction. The X direction and the Z direction are orthogonal to each other. The direction orthogonal to both of the Z direction and the X direction is defined as a Y direction. The Z direction and the Y direction rotate around the X direction when the imaging unit 30 is rotated around the center axis R. If the Z direction corresponds to a perpendicular direction, the Y direction is the left and right direction viewed from the patient when imaging is performed.

The placement surface 331 is orthogonal to the Z direction and parallel to the X direction and the Y direction. In other words, the placement surface 331 is a flat surface orthogonal in the imaging direction. An angle of the imaging direction with respect to the perpendicular direction (hereinafter, "imaging angle") α corresponds to an angle of the placement surface 331 with respect to the horizontal plane. The imaging angle α changes within the range between 0 to 90 degrees. When X-ray imaging is performed, the placement surface 331 is orthogonal to the chest wall of the subject, and the Y direction is parallel to the chest wall of the subject.

The compression plate 35 compresses the breast placed on the breast placement stage 33. The compression plate 35 is provided between the X-ray generator 32 and the breast placement stage 33. The compression plate 35 is movable with respect to the breast placement stage 33 in the Z direction. The compression plate 35 is made of a thermoplastic resin, for example. As a thermoplastic resin, for example, a polycarbonate or a transparent acrylic resin, which has a high mechanical strength and allows X-rays to pass, is used.

The compression plate 35 has a compression surface 351. The compression surface 351 faces the placement surface 331 of the breast placement stage 33. The compression surface 351 is a flat surface for compressing a breast B in conjunction with the placement surface 331. Being tilted in the Y direction with respect to the placement surface 331, the compression plate 35 moves in a direction toward the breast placement stage 33 sous to support the breast B placed on the placement surface 331 from below, and compress the breast B in conjunction with the placement surface 331. The compression plate 35 moves in a direction of approaching the placement surface 331, with the distance between the lower portion of the compression plate 35 and the placement surface 331 being shorter than the distance between the upper portion of the compression plate 35 and the placement surface 331.

The compression plate moving mechanism 36 consists of a moving mechanism and a driving unit. The compression plate moving mechanism 36 is connected to the compression plate 35, and moves the compression plate 35 in the Z direction with respect to the breast placement stage 33 so as to move the compression plate 35 in a direction closer to or away from the breast placement stage 33. The compression plate moving mechanism 36 is realized by a gear, a stepping motor, a belt conveyor, or a lead screw, etc., and is connected to the compression plate 35. If the compression plate 35 moves toward the breast placement stage 33 due to the action of the compression plate moving mechanism 36, the breast placed on the placement surface 331 of the breast placement stage 33 is compressed between the compression plate 35 and the breast placement stage 33. The breast B is flattened out by being compressed by the compression plate 35, and the superimposition of the mammary gland in the breast B is thereby reduced.

The compression plate tilting mechanism 37 consists of a tilting mechanism and a driving unit. The compression plate moving mechanism 36 is connected to the compression plate 35. The compression plate moving mechanism 36 adjusts an angle (hereinafter "a tilt angle") e, which is defined by the compression surface 351 of the compression plate 35 and the placement surface 331 of the breast placement stage 33 with respect to the Y direction, by changing the tilt of the compression plate 35 with respect to the breast placement stage 33. The tilt angle θ changes within the range of 0 to 90 degrees. The compression plate tilting mechanism 37 is realized by a gear, a stepping motor, a belt conveyor, and a lead screw, etc., for example, and is connected to the compression plate 35. The compression plate tilting mechanism 37 may be called a "tilt angle adjustment mechanism".

FIG. 3 is a diagram showing a configuration example of the compression plate 35, the compression plate moving mechanism 36, and the compression plate tilting mechanism 37. In the example shown in FIG. 3, the compression plate moving mechanism 36 is attached to the supporting arm 31, and is movable in the Z direction with respect to the supporting arm 31. The compression plate tilting mechanism 37 is constituted by two connecting members and a motor connected to each of the connecting members. Each of the connecting members is attached, at one of its edges, to the motor accommodated on the inside of the compression plate moving mechanism 36. The other edge of each connecting member is attached to the compression plate 35 at a location away from each other with respect to the Y direction. Thus, the compression plate 35 is connected to the compression plate moving mechanism 36 via the compression plate tilting mechanism 37. By the compression plate moving mechanism 36, the compression plate 35 and the compression plate tilting mechanism 37 move together in the Z direction closer to or further away from the breast placement stage 33. Each of the connecting members is movable with respect to the compression plate moving mechanism 36 in the Z direction. As a result of the two connecting members independently moving with respect to the compression plate moving mechanism 36, the tilt angle θ of the compression plate 35 changes.

The compression plate 35 may be connected to the compression plate tilting mechanism 37 via the compression plate moving mechanism 36. In this case, the compression plate tilting mechanism 37 is attached to the supporting arm 31, and the compression plate moving mechanism 36 is attached to the compression plate tilting mechanism 37. The compression plate 35 is attached to the compression plate moving mechanism 36. The compression plate tilting mechanism 37 causes the compression plate moving mechanism 36 and the compression plate 35 to rotate together with respect to the supporting arm 31. As a result, the tilt angle θ of the compression plate 35 changes, and the direction of moving of the compression plate 35 by the compression plate moving mechanism 36 changes from the Z direction. Then, the compression plate moving mechanism 36 causes the compression plate 35 to move closer to or away from the breast placement stage 33 with respect to the compression plate tilting mechanism 37 and the supporting arm 31.

The operation panel 38 is an input device for inputting a Z-direction movement of the compression plate 35, a target value θX of the tilt angle of the compression plate 35, instructions relating to the rotation of the imaging unit 30, etc.

The console apparatus 50 includes a memory 51, a display 52, an input interface 53, and processing circuitry 54. Hereinafter, the console apparatus 50 will be described as a device separate from the imaging apparatus 10; however, the console apparatus 50 or some of the structural elements thereof may be incorporated in the imaging apparatus 10.

Hereinafter, the console apparatus 50 will be described as an apparatus performing a plurality of functions with a single console; however, it is possible to perform a plurality of functions with separate consoles. For example, the functions of the processing circuitry 54, such as an image generating function 545 (described later) may be implemented on different console devices in a distributed manner.

The memory 51 is a storage device such as an HDD (hard disk drive), an SSD (solid state drive), or an integrated circuit storage unit, etc., configured to store various kinds of information. The memory 51 may be a portable storage medium, such as a CD (compact disc), a DVD (digital versatile disc), or a flash memory, other than an HDD or SDD, etc. Alternatively, the memory 51 may be a drive apparatus that writes and reads various types of information to and from a semiconductor memory, such as a flash memory or a random access memory (RAM), etc. The storage area of the memory 51 may be in the mammography apparatus 1, or in an external storage device connected via a network.

The memory 51 stores X-ray images, programs executed by the processing circuitry 54, and various types of data used for the processing in the processing circuitry 54, for example. The memory 51 is an example of a storage unit.

The display 52 displays various kinds of information. For example, the display 52 outputs medical images (X-ray images) generated by the processing circuitry 54, and a graphical user interface (GUI) or the like for receiving various types of operations from the operator. For example, the display 52 is a liquid crystal display or a CRT (cathode ray tube) display. The display 52 is an example of a display unit. The display 52 may be provided on the supporting unit 20 and the imaging apparatus 30, etc. The display 52 may be a desktop type, or comprised of a tablet device capable of wireless communications with the main body of the console apparatus 50, etc.

The input interface 53 accepts various kinds of input operations from the operator, converts the accepted input operations to electric signals, and outputs the electric signals to the processing circuitry 54. For example, the input interface 53 receives subject information, imaging conditions, inputs of various types of command signals, etc. from an operator. For example, the input interface 53 is realized by a track ball, a mouse, a keyboard, switches, buttons, a joy stick, a touch pad that allows input operations through a touch on an operation screen, a touch-panel display in which a display screen and a touch pad are integrated, or a foot switch, and the like, which are all designed for instructing the supporting arm 31 to move, setting an X-ray irradiation range, performing X-ray imaging, and various functions of the processing circuitry 54, etc. The input interface 53 is an example of an input unit and an operation unit. The input interface 53 may be provided on the supporting unit 20 and the imaging apparatus 30, etc. The input interface 53 may be configured as a tablet device capable of communicating wirelessly with the console apparatus 50. The interface 53 is not limited to a device having physical operational components, such as a mouse and a keyboard, etc. Examples of the input interface 53 include processing circuitry that receives an electric signal corresponding to an input operation from an external input device, which is provided separately from the apparatus, and that outputs the received electric signal to the processing circuitry 54. The input interface 53 is an example of an operation unit.

The processing circuitry 54 controls the entire operation of the mammography apparatus 1. The processing circuitry 54 is a processor that invokes a program in the memory 51 and performs a system controlling function 541, a tilt angle determination function 542, a drive controlling function 543, an X-ray controlling function 544, an image generating function 545, and a display controlling function 546.

FIG. 1 illustrates the case where the system controlling function 541, the tilt angle determination function 542, the drive controlling function 543, the X-ray controlling function 544, the image generating function 545, and the display controlling function 546 are realized in a single processing circuitry 54; however, the processing circuitry may be constituted by a combination of a plurality of independent processors, and the functions may be realized by the processors executing the programs. The system controlling function 541, the tilt angle determination function 542, the drive controlling function 543, the X-ray controlling function 544, the image generating function 545, and the display controlling function 546 may be respectively referred to as system controlling circuitry, tilt angle determination circuitry, drive controlling circuitry, X-ray controlling circuitry, image generation circuitry, and display controlling circuitry; furthermore, each of these functions may be implemented as individual hardware circuitry.

The term "processor" used in the above explanation means, for example, circuitry such as a CPU (central processing unit), a GPU (graphics processing unit), an ASIC, or a programmable logic device (for example, an SPLD (simple programmable logic device), a CPLD (complex programmable logic device), or an FPGA (field programmable gate array)). The processor realizes its function by reading and executing the program stored in the memory 51. A program may be directly integrated into the circuitry of the processor, instead of storing the program in the memory 51. In this case, the processor reads and executes a program integrated into the circuitry to realize the corresponding function. Each processor of the present embodiment is not limited to a case where each processor is configured as a single circuit; a plurality of independent circuits may be combined into one processor to realize the function of the processor. In addition, a plurality of structural elements in FIG. 1 may be integrated into one processor to realize the function. The above description of the "processor" is applicable to the subsequent embodiments and modifications.

The processing circuitry 54 controls, through the system controlling function 541, each of the plurality of structural elements of the mammography apparatus 1 based on an input operation received from the operator via the input interface 53. For example, the processing circuitry 54 controls the structural elements of the imaging apparatus 10 in accordance with imaging conditions. The processing circuitry 54 that enables the system controlling function 541 is an example of a system control unit.

The processing circuitry 54 determines, through the tilt angle determination function 542, a target value θX of the tilt angle of the compression plate 35 in accordance with the imaging angle α. In other words, the processing circuitry 54 determines the tilt angle of the compression plate 35 in accordance with the tilt angle of the breast placement stage 33. Specifically, the processing circuitry 54 determines a target value θX of the tilt angle of the compression plate 35 in accordance with the angle of the placement surface 331 with respect to the horizontal plane. At this time, if the imaging angle α is a first angle, the processing circuitry 54 sets the target value θX of the tilt angle to a first value, and if the imaging angle α is a second angle which is larger than the first angle, the processing circuitry 54 sets the target value θX of the tilt angle to a second value which is equal to or greater than the first value. In other words, as the imaging angle α becomes larger, the processing circuitry 54 sets the target value θX of the tilt angle to a larger value. The processing circuitry 54 that enables the tilt angle determination function 542 is an example of a tilt angle determination unit.

The processing circuitry 54 determines the target value θX of the tilt angle based on the correspondence table showing the relationship between the imaging angle α and the target value θX of the tilt angle. The correspondence table of the relationship between the imaging angle α and the target value θX of the tilt angle is for example a look-up table. The correspondence table of the relationship between the imaging angle α and the target value θX of the tilt angle is stored in the memory 51, for example. FIG. 4 is a diagram showing an example of a correspondence table of the relationship between the imaging angle α and the target value θX of the tilt angle. In the example shown in FIG. 4, θ8 is a value equal to or greater than θ7, θ7 is a value equal to or greater than θ6, θ6 is a value equal to or greater than θ5, θ5 is a value equal to or greater than θ4, θ4 is a value equal to or greater than θ3, θ83 is a value equal to or greater than θ2, and θ2 is a value equal to or greater than θ1.

The processing circuitry 54 controls, through the drive controlling function 543, each of the driving units based on, for example, information regarding the driving of each of the driving units, which is input from the input interface 53. Specifically, the processing circuitry 54 controls a driving unit for moving the rotation driving unit 41 for rotating the supporting axis 40, and the driving unit for moving the supporting breast placement stage 33. The processing circuitry 54 controls the compression plate moving mechanism 36 and the compression plate tilting mechanism 37 based on the target value θX of the tilt angle, so as to control the position of the compression plate 35, the tilt angle θ of the compression plate 35, and a pressure of compression of the breast between the compression plate 35 and the breast placement stage 33 (hereinafter "compression pressure"). The processing circuitry 54 that enables the drive controlling function 543 is an example of a drive controlling unit. The processing circuitry 54 controls the driving of the compression plate 35 so that the breast placed on the breast placement stage 33 tilted by the supporting arm 31 is compressed, while being supported from below. Specifically, the processing circuitry 54 controls the driving of the compression plate 35 so that the breast is compressed in a state where the angle of the compression plate 35 with respect to the horizontal plane is larger than the angle of the breast placement stage 33 with respect to the horizontal plane and the distance between the lower portion of the compression plate 35 and the breast placement stage 33 is shorter than the distance between the upper portion of the compression plate 35 and the breast placement stage 33.

The processing circuitry 54 reads, through the X-ray controlling function 544, for example, the information from the system controlling function 541, and controls the X-ray conditions, such as a tube current, a tube voltage, a focal-spot size, an irradiation time, a pulse width, and an X-ray irradiation range, etc. in the high-voltage generating apparatus 25. The processing circuitry 54 that enables the X-ray controlling function 544 is an example of an X-ray controlling unit.

The processing circuitry 54 generates, through the image generating function 545, an X-ray image based on data output from the X-ray detector 34, for example. The processing circuitry 54 may perform various types of synthesis processing or subtraction processing on the generated X-ray image. The processing circuitry 54 that enables the image generation function 545 is an example of an image generating unit.

The processing circuitry 54 reads, through the display controlling function 546, a signal from the system controlling function 541, and displays a desired X-ray image obtained from the memory 51 on the display 52. The processing circuitry 54 that enables the X-ray controlling function 546 is an example of a display controlling unit.

Next, an operation of the positioning process performed by the mammography apparatus 1 will be described. The positioning process is a process of compressing a breast between the breast placement stage 33 and the compression plate 35, while deviation of the breast from a correct position due to its own weight is suppressed during the breast positioning in the MLO-view imaging. The processing procedure in the positioning process which will be described below is merely an example, and the process can be changed as far as is reasonably possible. Omission, replacement, or addition of a step in the process procedure described hereinafter can be made as appropriate, in accordance with an actual situation where the present embodiment is realized.

Figure 5:
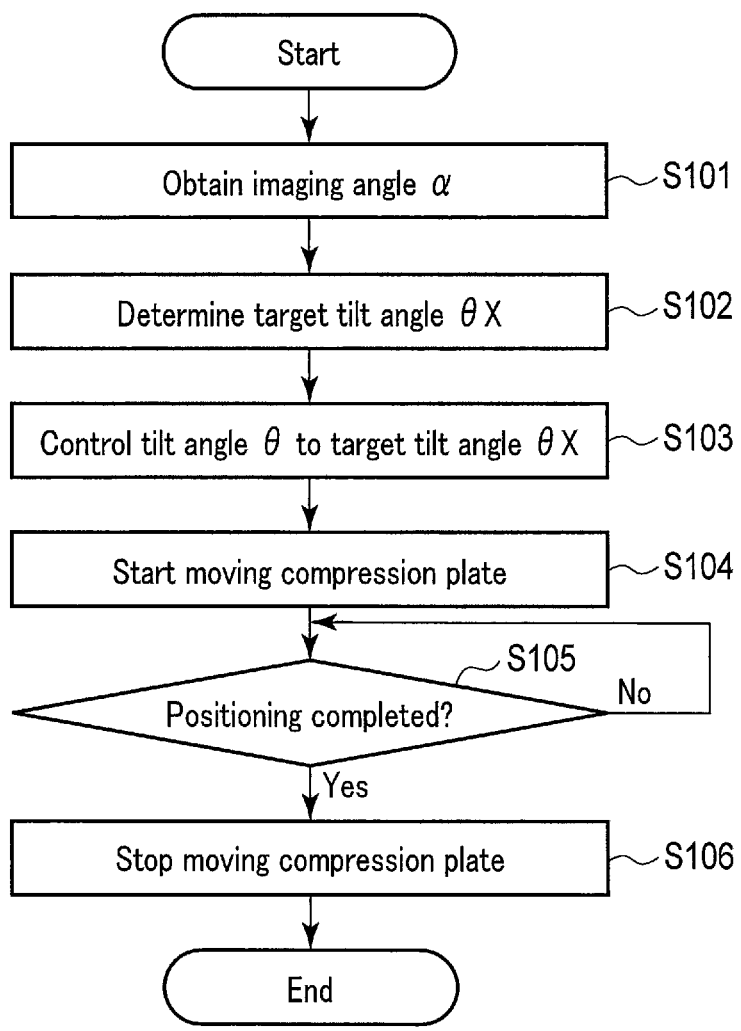
FIG. 5 is a flowchart illustrating a processing procedure of a positioning process performed by the mammography apparatus according to the first embodiment.
Figure 6:
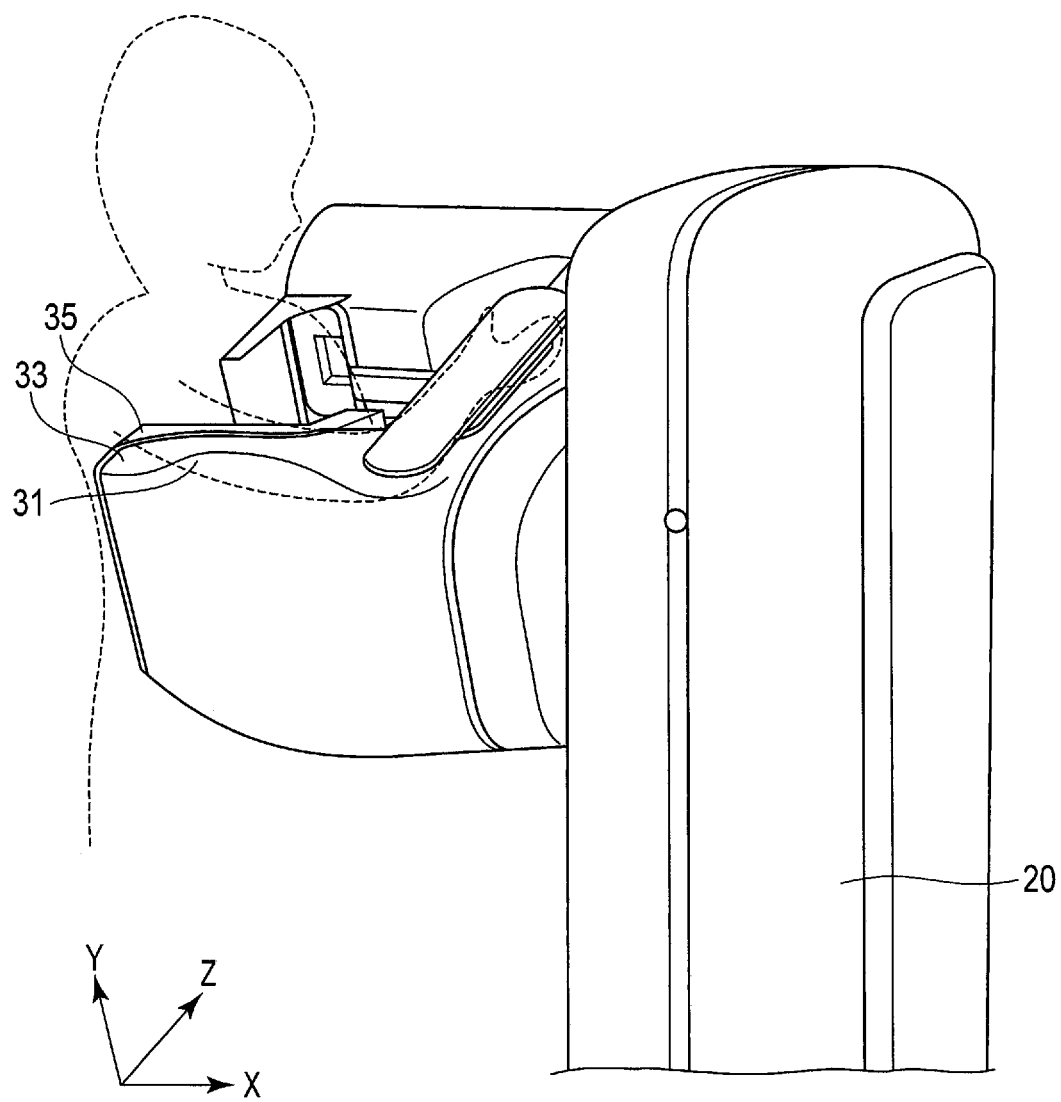
FIG. 6 is a perspective view illustrating MLO-view imaging by the mammography apparatus according to the first embodiment.
Figure 7:
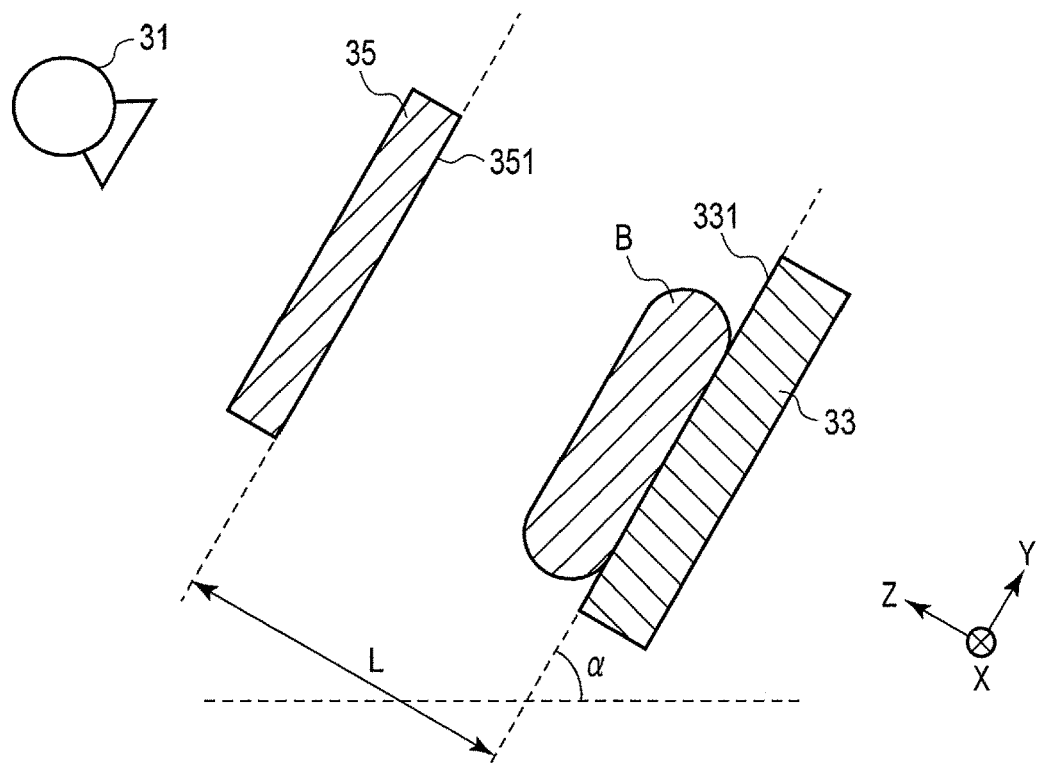
FIG. 7 is a schematic diagram explaining procedures of the positioning process according to the first embodiment.

FIG. 5 is a flowchart showing an example of a procedure of the positioning process according to the present embodiment. The positioning process is performed when the imaging unit 30 is rotated by the imaging angle α set for the MLO-view imaging, and a breast B of the patient is placed on the placement surface 331 of the breast placement stage 33, with the breast B being compressed against the breast placement stage 33 by a radiologic technologist by hand. The processing circuitry 54 commences the positioning process upon input of an instruction to commence a positioning via the input interface 53 or the operation panel 38. The radiologic technologist is an example of an operator. FIG. 6 is a perspective view illustrating the MLO view imaging, and it shows how the breast B of the patient is placed on the placement surface 331 of the breast placement stage 33. FIGS. 7 through 10 are schematic diagrams for explaining the procedures of the positioning process. FIG. 7 shows the patient's breast B in the state of being placed on the placement surface 331 of the breast placement stage 33 during the MLO-view imaging, in a cross section passing through the center of the detection surface of the X-ray detector 34 and the X-ray detector 32 and perpendicular to the rotation axis of the supporting arm 31.

(Positioning Process)

(Step S101)

Through the tilt angle determination function 542, the processing circuitry 54 obtains an imaging angle α. The processing circuitry 54 obtains the imaging angle α by obtaining an imaging method input via the input interface 53, for example.

(Step S102)

Through the tilt angle determination function 542, the processing circuitry 54 determines the target value θX of the tilt angle based on the obtained imaging angle α and the correspondence table showing the relationship between the imaging angle and the target value θX of the tilt angle.

(Step S103)

Figure 8:
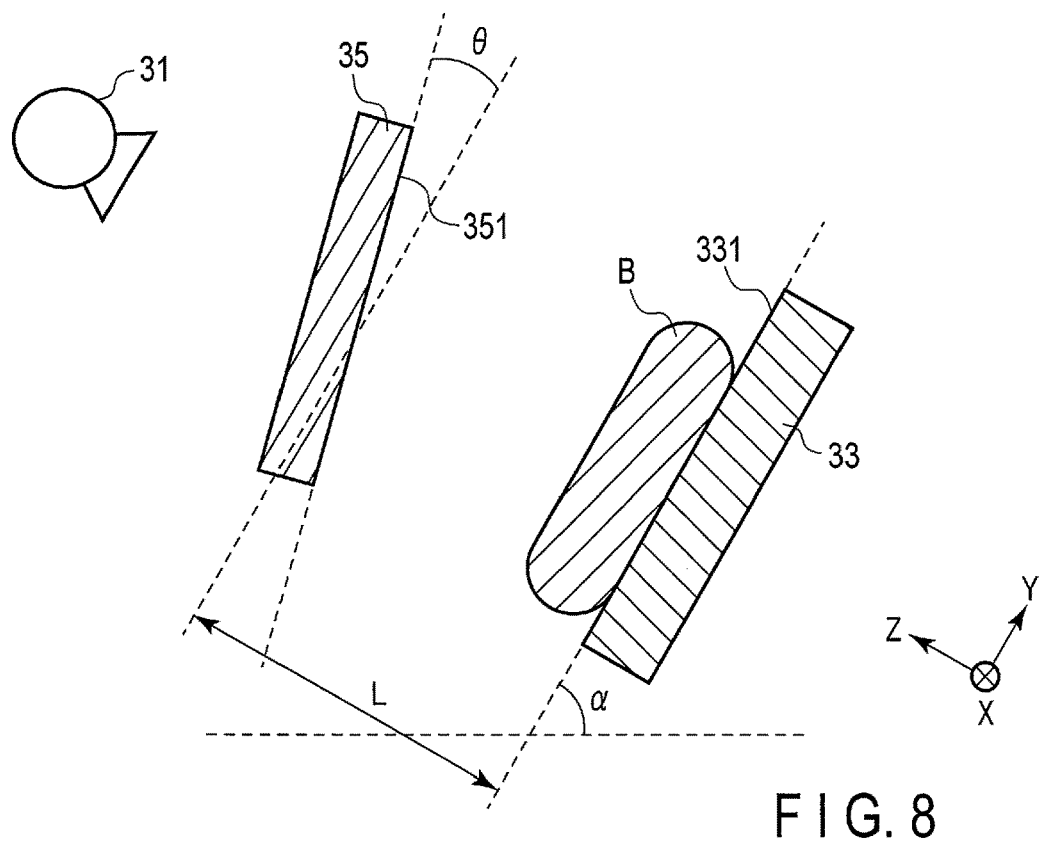
FIG. 8 is a schematic diagram explaining procedures of the positioning process according to the first embodiment.

Through the drive control function 543, the processing circuitry 54 controls the compression plate moving mechanism 36 and the compression plate tilting mechanism 37, and tilts the compression plate 35 with respect to the placement surface 331 of the breast placement stage 33 until the tilt angle θ becomes the target angle θX, as shown in FIG. 8. FIG. 8 shows the compression plate 35 in the state of being tilted at the target value θX of the tilt angle θ, which was originally in the state shown in FIG. 7, in a cross section passing through the center of the detection surface of the X-ray detector 34 and the X-ray generator 32 and perpendicular to the rotation axis of the supporting arm 31.

(Step S104)

Through the drive control function 543, the processing circuitry 54 causes the compression plate 35 to start moving in a direction toward the breast placement stage 33. The compression plate 35 gradually approaches the breast placement stage 33, with its compression surface 351 being tilted up to the target tilt angle θX with respect to the placement surface 331. Then, as the compression plate 35 approaches the breast placement stage 33, the distance L between the compression surface 351 and the placement surface 331 becomes shorter.

Figure 9:
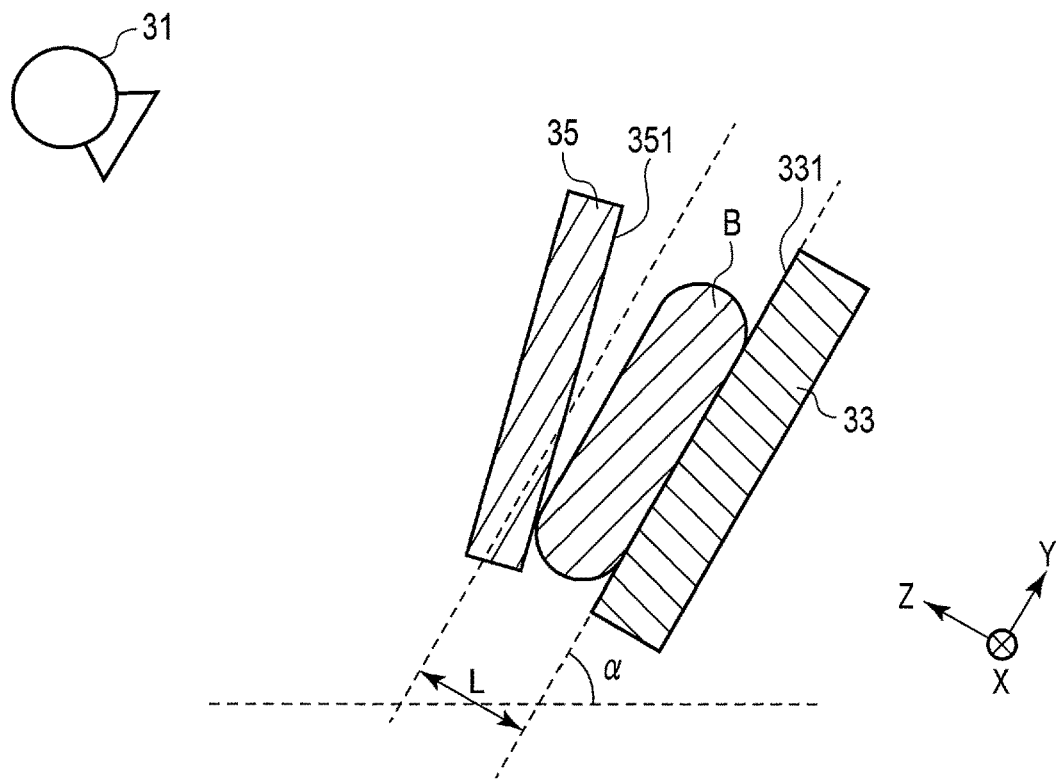
FIG. 9 is a schematic diagram explaining procedures of the positioning process according to the first embodiment.

When the compression plate 35 approaches the breast placement stage 33, first, the lower portion of the compression surface 351 of the compression plate 35 is brought into contact with the breast B, which is placed on the breast placement stage 33, from above, as shown in FIG. 9. FIG. 9 shows the state where the compression plate 35 becomes closer to the breast placement stage 33, which was originally in the state shown in FIG. 8, and the lower edge of the compression surface 351 is in contact with the breast B, in a cross section passing through the center of the detection surface of the X-ray detector 34 and the X-ray generator 32 and perpendicular to the rotation axis of the supporting arm 31.

Figure 10:
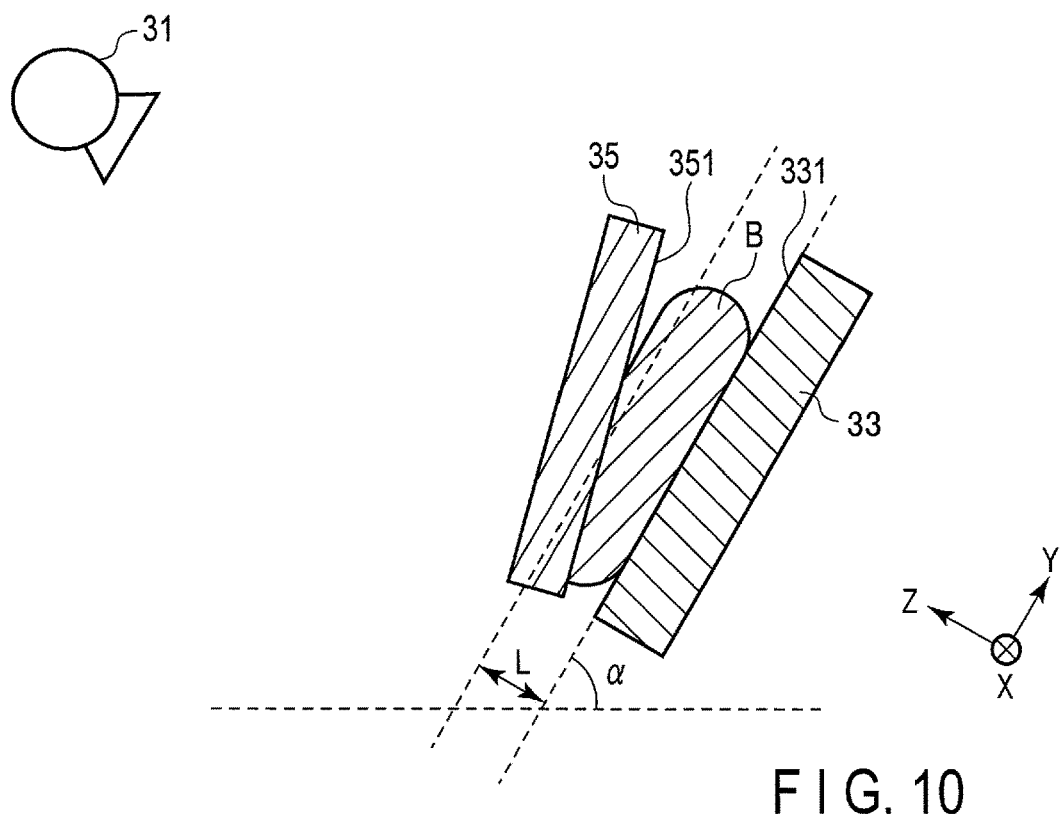
FIG. 10 is a schematic diagram explaining procedures of the positioning process according to the first embodiment.

As the compression plate 35 further approaches the breast placement stage 33, as shown in FIG. 10, the area where the compression surface 351 is in contact with the breast B is increased and the compression pressure becomes greater; as a result, the breast B is flattened out on the placement surface 331. Then, when the breast B is sufficiently compressed, the radiologic technologist determines that the positioning of the breast B is completed, and for example inputs an instruction to stop the moving of the compression plate 35 through the input interface 53 or the operation panel 38. FIG. 10 shows the breast B in the state of being fully compressed as a result of the moving of the compression plate 35, which was originally in the state shown in FIG. 9, in a direction of approaching the breast placement stage 33, in a cross section passing through the center of the detection surface of the X-ray detector 34 and the X-ray generator 32 and perpendicular to the rotation axis of the supporting arm 31.

(Step S105)

Through the driving control function 543, the processing circuitry 54 determines whether or not an instruction to stop the moving of the compression plate 35 is input. When the instruction to stop the moving of the compression plate 35 is not input (No in step S105), the processing circuitry 54 waits until the instruction to stop the moving of the compression plate 35 is input and continues the process of moving the compression plate 35 closer to the breast placement stage 33. If the instruction to stop the moving of the compression plate 35 is input (Yes in step S105), the processing proceeds to step S106.

(Step S106)

Through the drive control function 543, the processing circuitry 54 stops the moving of the compression plate 35 in the direction of approaching the breast placement stage 33, and finishes the positioning process.

When the positioning process is finished, the radiologic technologist performs X-ray imaging on the breast B placed on the breast placement stage 33 and compressed by the compression plate 35, and obtains an X-ray image of the breast B.

In the following, advantageous effects of the mammography apparatus 1 according to the present embodiment are described.

The mammography apparatus 1 according to the present embodiment includes: an X-ray tube that generates X-rays; an X-ray detector 34 that detects X-rays irradiated from the X-ray tube; a breast placement stage 33 that has a placement surface 331 on which a subject's breast is placed and that supports the breast; a compression plate 35 provided between the X-ray tube and the breast placement stage 33, movable in a first direction orthogonal to the placement surface 331, and having a compression surface 351 facing the placement surface 331 and capable of compressing a breast in conjunction with the placement surface 331; a compression plate moving mechanism 36 that moves the compression plate 35 in the first direction; a compression plate tilting mechanism 37 that adjusts a tilt angle θ of the compression plate 35 with respect to the placement surface 331 in a second direction; and a supporting arm 31 that supports, with the placement surface 331 being tilted with respect to the horizontal plane, the X-ray tube, the breast placement stage 33, the X-ray detector 34, and the compression plate 35. Being tilted in the second direction, which is orthogonal to the first direction and parallel to the chest wall of the subject, with respect to the placement surface 331 through the tilt angle adjustment, the compression plate 35 moves in a direction toward the placement surface 331 so as to support the breast B from below in conjunction with the placement surface 331 and compress the breast B between the placement surface 331 and the compression plate 35.

Herein, the second direction is a direction orthogonal to a straight line connecting the X-ray generator 32 to the X-ray detector 34. The placement surface 331 is a flat surface orthogonal to the chest wall of a subject.

In the mammography apparatus 1 of the present embodiment, the compression plate 35 moves in a direction of approaching the placement surface 331, with the state that the distance between the lower portion of the compression plate 35 and the placement surface 331 being shorter than the distance between the upper portion of the compression plate 35 and the placement surface 331.

The Z direction corresponds to the first direction, and the Y direction corresponds to the second direction.

In other words, with the above-described configuration and operation, according to the mammography apparatus 1 of the present embodiment, the compression plate 35 moves toward the breast placement stage 33, being tilted in the left and right direction as viewed from the front (the patient's side), and thus the compression surface 351 can support a breast from below on the portion contacting the breast, and the breast can be compressed between the compression surface 351 and the placement surface 331. For this reason, a breast becomes less prone to falling from a predetermined position under its own weight when breast positioning takes place, and deviation from correct positioning caused by its own weight can be suppressed. Furthermore, image quality of an X-ray image is improved through the suppression of deviation from a correct position caused by the weight of the breast. The suppression of deviation from a correct position caused by the weight of the breast lessens a required power for a radiologic technologist's hand-compressing of a breast, and reduces the fatigue of the radiologic technologist.

The mammography apparatus 1 of the present embodiment has a supporting unit 20 that is installed on a floor surface or a wall surface of an examination room, and that supports the supporting arm 31. The supporting arm 31 rotates around the rotation axis orthogonal to the first and second directions with respect to the supporting unit 20. The mammography apparatus 1 of the present embodiment determines the target tilt angle θX in accordance with the imaging angle α, and if the imaging angle α is a first angle, the mammography apparatus 1 sets the target value θX of the tilt angle to a first value, and if the imaging angle α is a second angle which is larger than the first angle, the mammography apparatus 1 sets the target value θX of the tilt angle to a second value which is greater than the first value. Herein, the supporting unit 20 corresponds to a supporting stage, the center axis R of the supporting axis 40 corresponds to a rotation axis, and the imaging angle α corresponds to an angle of the placement surface 331 with respect to the horizontal plane.

In other words, with the above-described configuration and operation, according to the mammography apparatus 1 of the present embodiment, if the rotation angle of the imaging unit 30 in the X-ray imaging is large, the compression plate 35 can be more tilted with respect to the breast placement stage 33 when positioning of a breast placed on the breast placement stage 33 is performed. Thus, the larger an influence of the tilting of the placement surface 331 of the breast placement stage 33 during the X-ray imaging is on breast positioning, the more a tilt angle of the compression plate 35 with respect to the breast placement stage 33 can be increased, and it is thereby possible to effectively suppress deviation of a breast from correct positioning due to its own weight.

Second Embodiment

Next, the second embodiment will be described. The present embodiment is a modification of the configuration of the first embodiment as will be described below. In the present embodiment, the mammography apparatus 1 adjusts a tilt angle θ of the compression plate 35 in accordance with a distance between the compression plate 35 and the breast placement stage 33. Descriptions of the configurations, operations, and advantageous effects similar to those of the first embodiment will be omitted.

The processing circuitry 54 obtains, through the drive control function 543, a distance L between the compression surface 351 of the compression plate 35 and the placement surface 331 of the breast placement stage 33 over time. To obtain a distance L, the processing circuitry 54 calculates a distance L based on information regarding the driving state of the moving driving unit of the compression plate moving mechanism 36 and the driving state of the driving unit of the breast placement stage 33.

Figure 11:
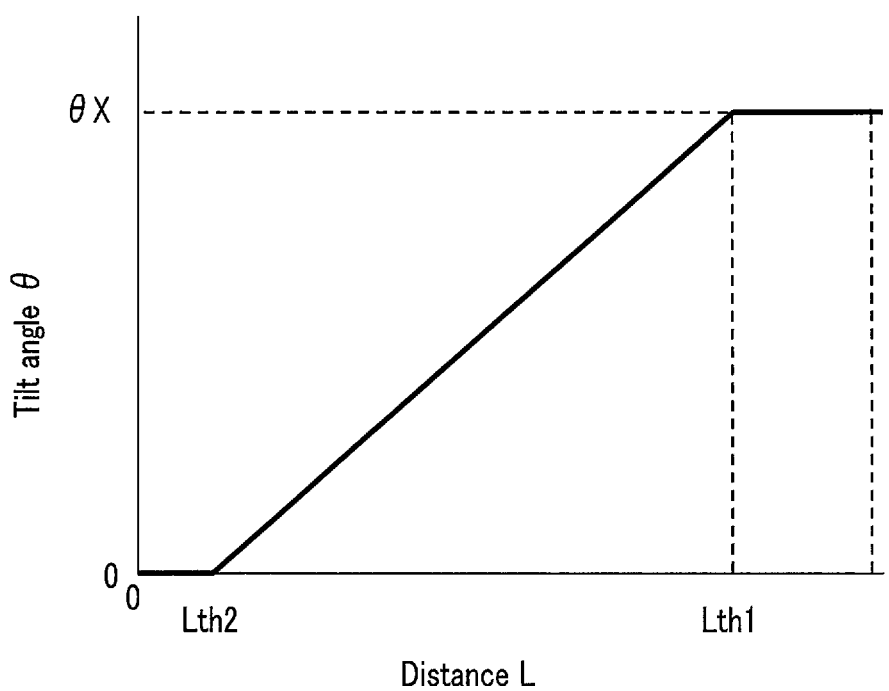
FIG. 11 is a diagram illustrating a relationship between a distance and a tilt angle between a breast supporting stage and a compression plate when a positioning process is performed by a mammography apparatus according to a second embodiment.

The processing circuitry 54 controls, through the drive control function 543, the tilt angle θ of the compression plate 35 in accordance with a distance. L. FIG. 11 is a diagram illustrating a relationship between the distance L and a tilt angle θ at the time of performing a positioning process. In FIG. 11, the horizontal axis indicates a distance L, and the vertical axis indicates a tilt angle θ. The processing circuitry 54 first determines whether or not the distance L between the compression surface 351 of the compression plate 35 and the placement surface 331 of the breast placement stage 33 is larger than a first threshold Lth1. If the distance L is larger than the first threshold Lth1, the processing circuitry 54 moves the compression plate 35 toward the breast placement stage 33 in a state where the tilt angle θ of the compression plate 35 is a target angle θX. If the distance L is equal to or less than the first threshold Lth1 on the other hand, the processing circuitry 54 moves the compression plate 35 toward the breast placement stage 33 in a state where the tilt angle θ is smaller than the target angle θX. The first threshold Lth1 is a value in the range of 30 to 50 mm, for example. The first threshold Lth1 is stored in a memory 51, for example.

The processing circuitry 54 controls the compression plate moving mechanism 36 and the compression plate tilting mechanism 37 in such a manner that the tilt angle θ becomes 0 if the distance L is a second threshold Lth2. If the distance L is equal to or less than the second threshold Lth2, the processing circuitry 54 causes the compression plate 35 to move toward the breast placement stage 33, with the tilt angle θ of the compression plate 35 being at 0. The second threshold Lth2 is a value smaller than the first threshold Lth1. The second threshold Lth2 is a value in the range of 10 to 30 mm, for example. The second threshold Lth2 is stored in a memory 51, for example.

Figure 12:
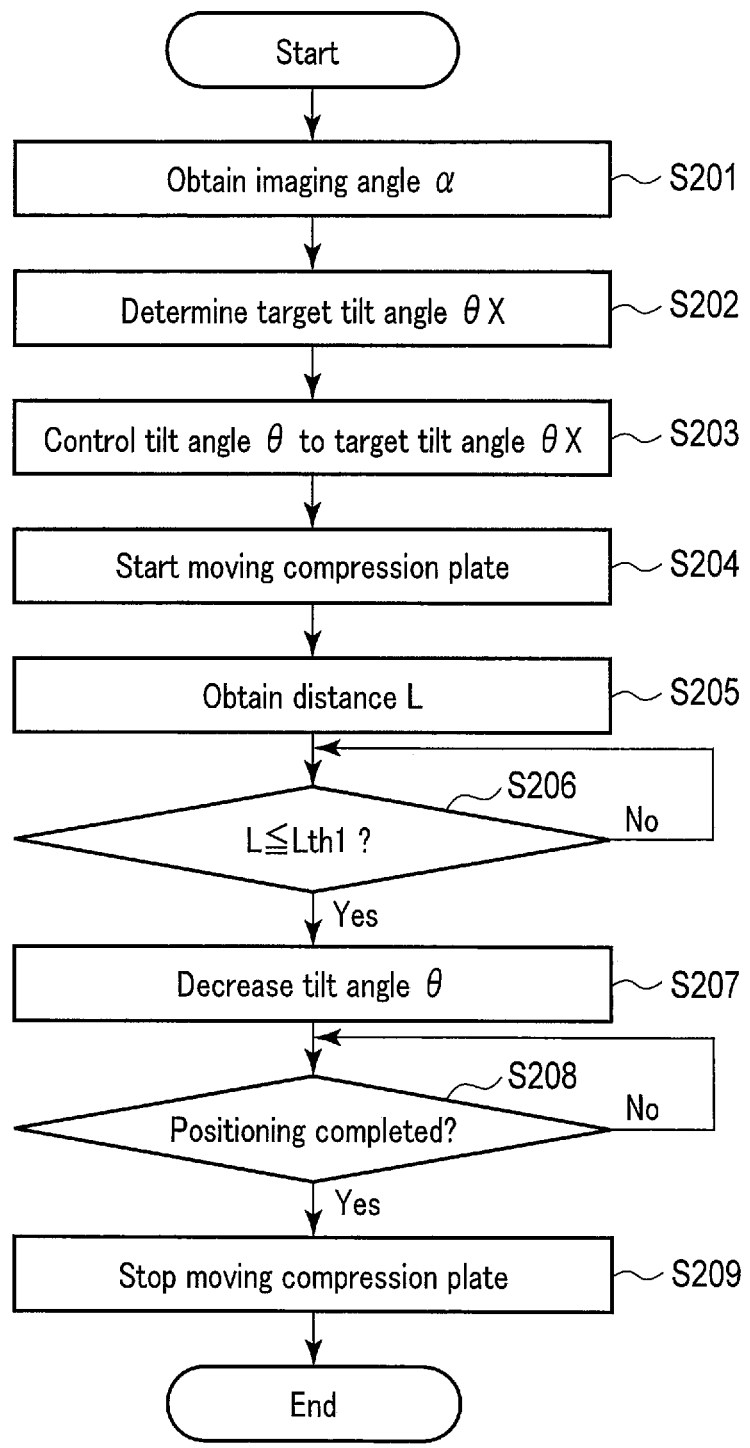
FIG. 12 is a flowchart illustrating an example of procedures of the positioning process performed by the mammography apparatus according to the second embodiment.
Figure 13:
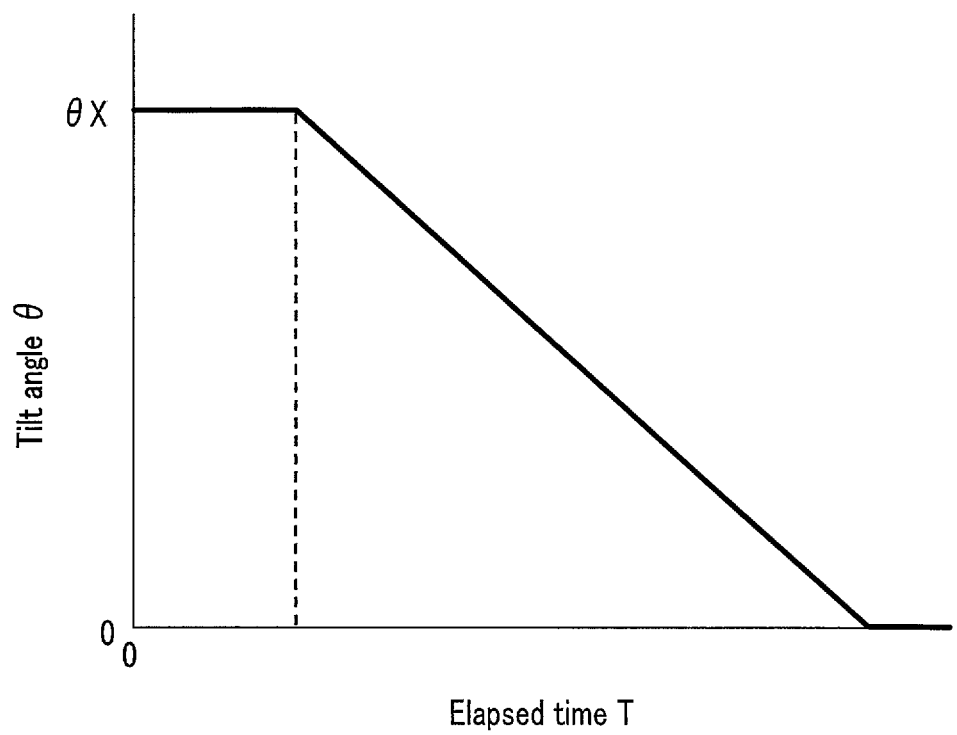
FIG. 13 is a diagram illustrating a relationship between a length of time that has elapsed since the positioning process started and the tilt angle according to the second embodiment.

Next, an operation of positioning performing process performed by the mammography apparatus 1 will be described. FIG. 12 is a flowchart showing an example of a procedure of the positioning process according to the present embodiment. Since the process in step S201 through step S204 and step S208 through step S209 in FIG. 12 is the same as the process in step S101 through step S106 in the first embodiment, descriptions thereof are omitted. FIG. 13 is a diagram illustrating a relationship between a length of time T that has elapsed since the positioning process (hereinafter "elapsed time") and a tilt angle θ. In FIG. 13, the horizontal axis indicates an elapsed time T, and the vertical axis indicates a tilt angle θ.

(Positioning Process)

(Step S205)

Through the drive control function 543, the processing circuitry 54 obtains a distance L between the compression surface 351 of the compression plate 35 and the placement surface 331 of the breast placement stage 33.

(Step S206)

Through the drive control function 543, the processing circuitry 54 determines whether or not the distance L is equal to or less than the first threshold Lth1. If the distance L is not equal to or less than the predetermined first threshold Lth1, in other words, if the distance L is greater than the first threshold Lth1 (No in step S206), the processing circuitry 54 causes the compression plate 35 to move toward the breast placement stage 33 with the tilt angle θ of the compression plate 35 being a target angle θX until the distance L becomes equal to or less than the first threshold Lth1. If the distance L is equal to or less than the first threshold Lth1 (Yes in step S206), the processing proceeds to step S207.

(Step S207)

Through the drive control function 543, the processing circuitry 54 causes the compression plate 35 to move toward the breast placement stage 33 and to gradually decrease the tilt angle θ of the compression plate 35. For this reason, if the distance L is equal to or less than the first threshold Lth1, the tilt angle θ becomes smaller than the target angle θX. When the distance L is equal to or less than the second threshold Lth2 on the other hand, the processing circuitry 54 moves the compression plate 35 toward the breast placement stage 33 in a state where the tilt angle θ is 0.

In the following, advantageous effects of the mammography apparatus 1 according to the present embodiment are described. In the present embodiment, advantageous effects can be achieved in addition to those of the first embodiment.

For example, if an imaging target is a large breast, positioning deviation tends to occur due to the weight of the breast. If an imaging target is a large breast in the state where the distance L is greater than the first threshold Lth1, the breast placed on the breast placement stage 33 is in contact with the compression plate 35. Under the state where the distance L is equal to or less than the first threshold Lth1 and greater than the second threshold Lth2, the breast is compressed by the compression plate 35, and the radiologic technologist retracts his hand that has been supporting the breast. When the distance L is equal to or less than the second threshold Lth2, the breast is in a fully compressed state.

On the other hand, if an imaging target is a small breast, the positioning deviation due to the weight of the breast occurs less easily. If an imaging target is a small breast in the state where the distance L is equal to or less than the first threshold Lth1 and greater than the second threshold Lth2, the breast placed on the breast placement stage 33 is in contact with the compression plate 35. Under the state where the distance L is equal to or less than the second threshold Lth2, the breast is compressed by the compression plate 35, and the radiologic technologist retracts his hand that has been supporting the breast.

The mammography apparatus 1 of the present embodiment controls the driving of the compression plate tilting mechanism 37 and the driving of the compression plate moving mechanism 36 based on the target angle θX, and if the distance L between the compression plate 35 and the breast placement stage 33 is greater than the first threshold Lth1, the compression plate 35 moves toward the breast placement stage 33, with the tilt angle θ being the target angle θX, and if the distance L is equal to or less than the first threshold Lth1, the compression plate 35 moves toward the breast placement stage 33, with the tilt angle θ being smaller than the target angle θX. Herein, the first threshold Lth1 corresponds to a predetermined value. In other words, with the above-described configuration and operation, according to the mammography apparatus 1 of the present embodiment, if the imaging target is a large breast, the breast is compressed by the compression plate 35 in the state where the tilt angle θ is the target angle θX if the distance L is equal to or less than the first threshold Lth1 and greater than the second threshold Lth2. In this case, similarly to the first embodiment, it is possible to suppress deviation of the breast from a correct position due to its own weight. If the imaging target is a small breast on the other hand, the breast is compressed by the compression plate 35 in the state where the tilt angle θ is 0 if the distance L is equal to or less than the second threshold Lth2. Accordingly, in the case where the imaging target is a large breast or the positioning deviation tends to occur due to the weight of the breast, the deviation of the breast from a correct position can be suppressed by performing positioning with the compression plate 35 being tilted with respect to the breast placement stage 33; on the other hand, in the case where the positioning deviation does not easily occur because, for example, an imaging target is the small breast, the accuracy of the X-ray imaging can be improved by performing the positioning with the compression plate 35 not being tilted with respect to the breast placement stage 33.

A pressure acting on the breast may be used instead of the distance L between the compression plate 35 and the breast placement stage 33. In this case, a pressure sensor for detecting a pressure acting on the breast is provided in the compression plate 35, for example. The processing circuitry 54 that enables the drive control function 543 obtains a pressure detected by the pressure sensor, and if the pressure detected by the pressure sensor becomes a predetermined value, controls the driving of the compression plate 35 in such a manner that the tilt angle of the compression plate 35 coincides with the tilt angle of the breast placement stage 33. Specifically, the processing circuitry 54 controls the tilt angle θ of the compression plate 35 to 0 if the pressure detected by the pressure sensor becomes greater than the predetermined value. When the tilt angle θ of the compression plate 35 becomes 0, the tilt angle of the compression plate 35 with respect to the horizontal plane coincides with the tilt angle of the breast placement stage 33 with respect to the horizontal plane. In this state, the processing circuitry 54 causes the compression plate 35 to move toward the breast placement stage 33.

Third Embodiment

Figure 14:
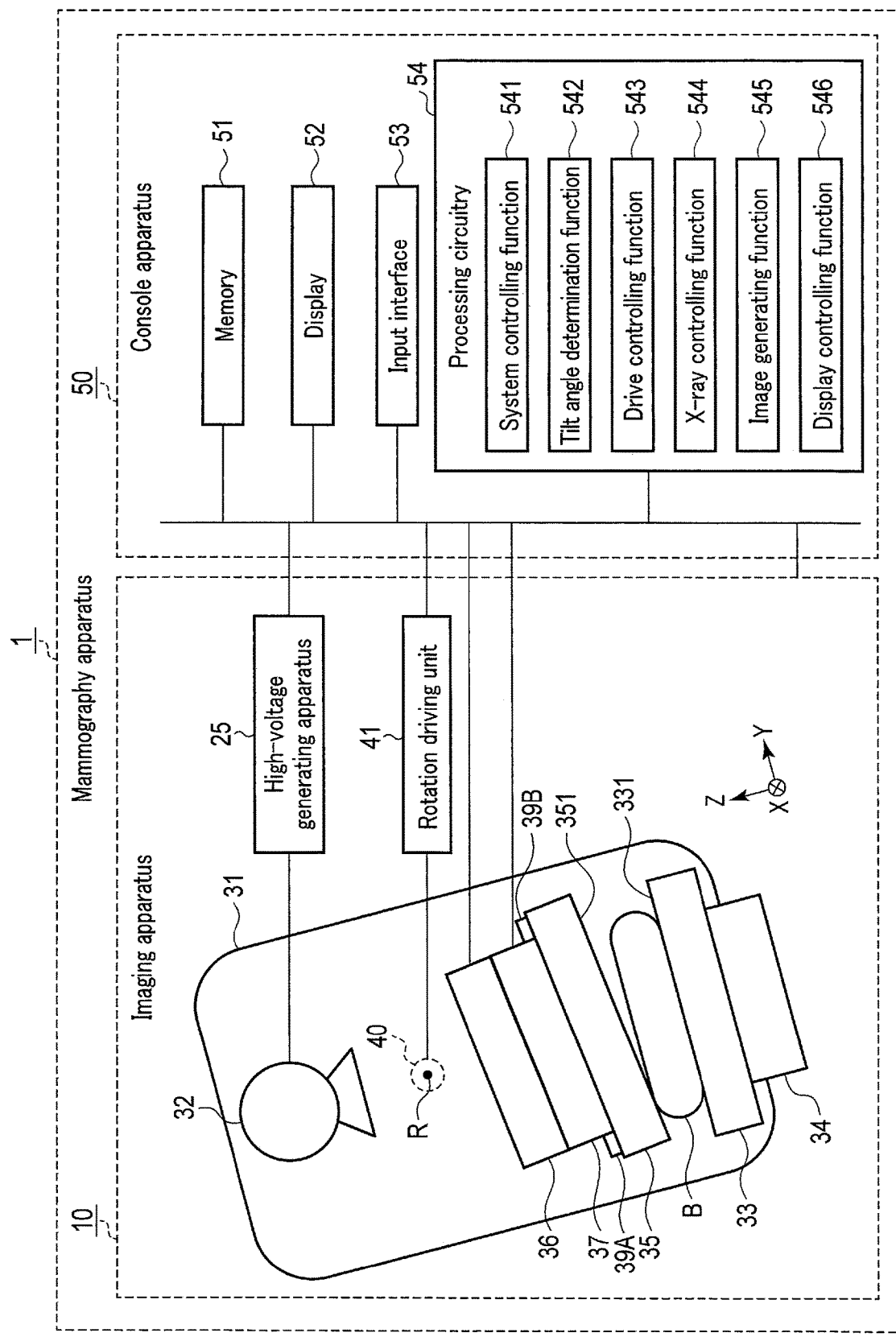
FIG. 14 is a diagram illustrating a configuration of a mammography apparatus according to a third embodiment.

Next, the third embodiment will be described. The present embodiment is a modification of the configuration of the first embodiment as will be described below. In the present embodiment, the mammography apparatus 1 includes a pressure sensor that detects a pressure acting on the compression plate 35 from the breast B, and adjusts a tilt angle θ of the compression plate 35 based on a detection result of the pressure at the pressure sensor and controls the compression pressure. Descriptions of the configurations, operations, and advantageous effects similar to those of the first embodiment will be omitted. FIG. 14 is a diagram illustrating a configuration of the mammography apparatus 1 according to the third embodiment. As shown in FIG. 14, a sensor 39A and a sensor 39B are attached to the compression plate 35. The sensor 39A is attached to a lower position in the compression plate 35, and is a pressure sensor for detecting a pressure P1 acting on the lower position of the compression surface 351. The sensor 39B is attached to an upper position in the compression plate 35, and is a pressure sensor for detecting a pressure P2 acting on the upper position of the compression surface 351. The pressure P1 and the pressure P2 are sent to the processing circuitry 54.

The processing circuitry 54 determines, through the drive control function 543, whether or not the breast B placed on the breast placement stage 33 is in contact with the compression plate 35 in accordance with the detection results of the sensor 39A and the sensor 39B. Then, the processing circuitry 54 controls the compression pressure acting on the breast B through the control of the tilt angle θ of the compression plate 35 in accordance with the state of contact between the breast B and the compression plate 35. Specifically, if the pressure P1 detected by the sensor 39A or the pressure P2 detected by the sensor 39B is greater than a predetermined value, the processing circuitry 54 causes the compression plate 35 to move toward the breast placement stage 33, and gradually increases the tilt angle θ of the compression plate 35 then gradually decreases the tilt angle θ. The predetermined value is for example 0[N]. The predetermined value is stored in the memory 51, for example. The predetermined value may be 0 or greater.

Figure 16:
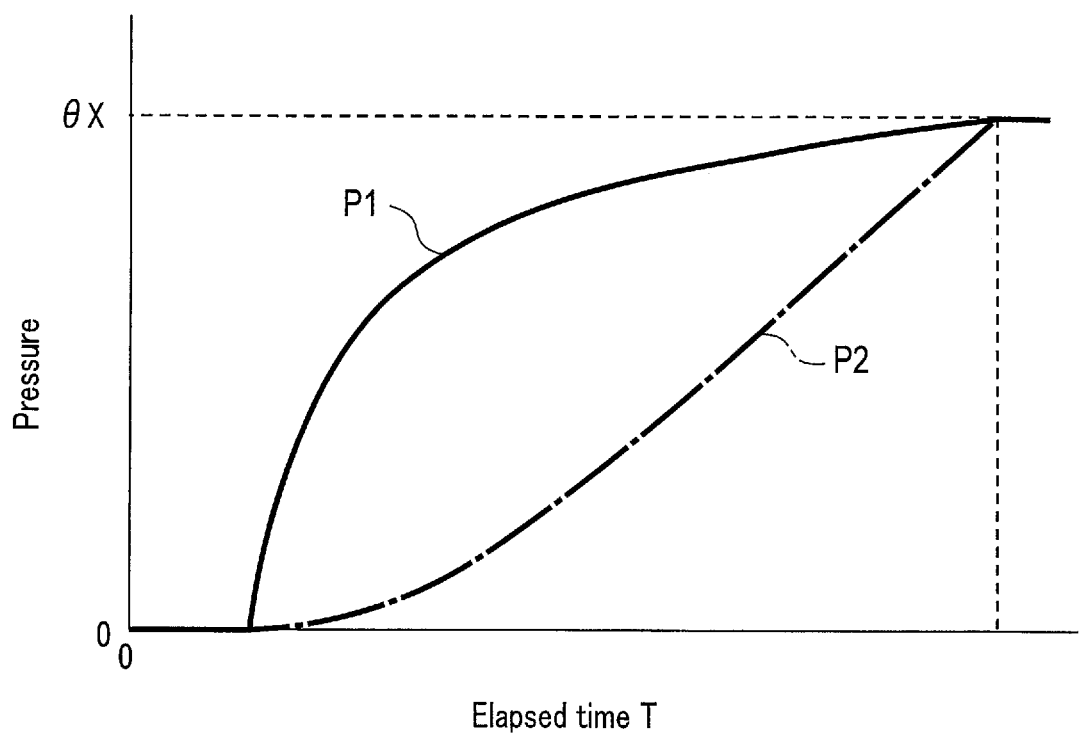
FIG. 16 is a diagram illustrating a relationship between a length of time that has elapsed since the positioning process started and a pressure detected by a sensor according to the third embodiment.

Next, an operation of positioning process performed by the mammography apparatus 1 will be described. FIG. 15 is a flowchart showing an example of a procedure of the positioning process according to the present embodiment. Since the process in step S301 through step S304 and step S308 through step S309 in FIG. 15 is the same as the process in step S101 through step S106 in the first embodiment, descriptions thereof are omitted. FIG. 16 is a diagram illustrating a relationship between a length of time T that has elapsed in the positioning process, and the pressure P1 detected by the sensor 39A and the pressure P2 detected by the sensor 39B. In FIG. 16, the horizontal axis indicates the elapsed time T, and the vertical axis indicates the pressure.

(Positioning Process)

(Step S304)

Through the driving control function 543, the processing circuitry 54 causes the compression plate 35 to start moving in a direction toward the breast placement stage 33. The compression plate 35 gradually approaches the breast placement stage 33 in the state where the tilt angle θ of the compression surface 351 is 0, in other words, the compression surface 351 is not tilted with respect to the placement surface 331. Then, as the compression plate 35 becomes closer to the breast placement stage 33, the distance L between the compression surface 351 and the placement surface 331 becomes less. When the compression plate 35 approaches the breast placement stage 33, the compression surface 351 of the compression plate 35 is brought into contact with the breast B, which is placed on the breast placement stage 33, from above. Until the compression plate 35 is brought into contact with the breast B, the pressure P1 and the pressure P2 remain 0.

(Step S305)

Through the driving control function 543, the processing circuitry 54 obtains the pressure P1 detected by the sensor 39A and the pressure P2 detected by the sensor 39B.

(Step S306)

Through the driving control function 543, the processing circuitry 54 determines whether or not the pressure P1 is greater than 0. If the pressure P1 is not greater than 0, in other words, if the pressure P1 is 0 (No in step S306), the processing circuitry 54 determines that the breast B is not in contact with the compression plate 35, and causes the compression plate 35 to move toward the breast placement stage 33 in the state where the tilt angle θ of the compression plate 35 is 0 until the pressure P1 becomes a value of 0 or greater. If the pressure P1 is greater than 0 (Yes in step S306), the processing circuitry 54 determines that the breast B is in contact with the compression plate 35, and the processing proceeds to step S307.

(Step S307)

Through the driving control function 543, the processing circuitry 54 that enables the drive control function 543 causes the compression plate 35 to move toward the breast placement stage 33 and gradually increases the tilt angle θ. As the tilt angle θ is gradually increased, the lower portion of the compression plate 35 gradually becomes closer to the breast placement stage 33 than the upper portion of the compression plate 35. Between the compression plate 35 and the breast placement stage 33, the breast B in the lower position is compressed to a greater extent than in the upper position. For this reason, the pressure P1 becomes greater than the pressure P2. An increment of the pressure P1 per unit of time is greater than an increment of the pressure P2 per unit of time.

When the tilt angle θ reaches the target angle θX, the processing circuitry 54 causes the compression plate 35 to move toward the breast placement stage 33, and gradually decreases the tilt angle θ. As the tilt angle θ is decreased, the difference between the distance from the upper portion of the compression plate 35 to the breast placement stage 33 and the distance from the lower portion of the compression plate 35 to the breast placement stage 33 becomes smaller. Thus, the difference between the pressure P1 and the pressure P2 becomes gradually smaller. Then, if a predetermined length of time is further elapsed, the processing circuitry 54 sets the tilt angle θ to 0. When the tilt angle θ becomes 0, the compression plate 35 is no longer tilted with respect to the breast placement stage 33, and the pressure P1 and the pressure P2 become approximately the same. The tilt angle θ may be controlled in accordance with, for example, the pressure P1, the distance L, or the elapsed time T, instead of the target tilt angle θX.

In the following, advantageous effects of the mammography apparatus 1 according to the present embodiment are described. In the present embodiment, advantageous effects can be achieved in addition to those of the first embodiment.

The mammography apparatus 1 of the present embodiment includes the sensors 39A and 39B that detect a pressure acting on the compression surface 351 or the placement surface 331, and if the pressures P1 and P2 detected by the sensors 39A and 39B are greater than predetermined values, the mammography apparatus 1 causes the compression plate 35 to move toward the breast placement stage 33 and gradually increases the tilt angle θ, then gradually decreases the tilt angle θ.

In other words, with the above-described configuration and operation, according to the mammography apparatus 1 of the present embodiment, when the breast placed on the breast placement stage 33 is in contact with the compression plate 35, the compression plate 35 is tilted with respect to the breast placement stage 33. Then, the compression plate 35 moves toward the breast placement stage 33 while being tilted with respect to the breast placement stage 33, the compression surface 351 supports the breast from below in the portion contacting the breast, and the breast is compressed in the state where the compression pressure in the lower portion is greater than the compression pressure in the upper portion. For this reason, advantageous effects similar to those of the first embodiment can be achieved.

With the above-described configuration and operation, according to the mammography apparatus 1 of the present embodiment, a breast is irradiated with X-rays to perform X-ray imaging, with the compression plate 35 not being tilted with respect to the breast placement stage 33. In other words, the X-ray imaging can be performed on a breast compressed to a uniform thickness. It is thereby possible to make uniform an X-ray dose received by a breast irrespective of the compression position, and to improve image quality of an X-ray image generated by X-ray imaging.

In this case, the mammography apparatus 1 is only required to be capable of determining whether or not the breast B placed on the breast placement stage 33 is compressed based on the compression pressure acting on the breast B. For example, the mammography apparatus 1 may include only one sensor. In this case, the sensor detects a torque acting on the compression plate 35. The processing circuitry 54 determines whether or not the breast B is in contact with the compression plate 35 based on a detection result of the sensor. When it is determined that the breast B is in contact with the compression plate 35, the processing circuitry 54 controls the tilt angle θ of the compression plate 35 in accordance with a predetermined flow of control stored in the memory 51 to control the compression pressure acting on the breast B.

The sensor may be attached to the breast placement stage 33. In this case, the sensor detects a pressure acting on the placement surface 331 of the breast placement stage 33. The processing circuitry 54 determines whether or not the breast is compressed based on a pressure value detected by the sensor.

Application Examples of First to Third Embodiments

The configurations of the mammography apparatus 1 in the first through third embodiments are applicable to an apparatus other than the mammography apparatus that performs the MLO-view imaging. The MLO-view imaging is an example of an imaging method in which imaging is performed with an imaging direction being tilted from the horizontal plane. The configurations described in the first through third embodiments are applicable to a mammography apparatus, as long as it performs breast positioning while being tilted with respect to the horizontal plane.

According to at least one of the foregoing embodiments, it is possible to prevent a breast from deviating from a correct position due to its own weight when breast positioning is carried out.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A mammography apparatus, comprising:
a breast placement stage comprising a placement surface on which a breast is placed;
a compression plate that compresses the breast placed on the breast placement stage;
a supporting arm that supports the breast placement stage in such a manner that the stage can be tilted; and
processing circuitry configured to:
control driving of the compression plate in such a manner that the breast placed on the breast placement stage tilted by the supporting arm is supported from below and compressed,
determine a tilt angle of the compression plate in accordance with a tilt angle of the breast placement stage,
set the tilt angle of the compression plate to a first value when an angle of the placement surface with respect to a horizontal plane makes a first angle,
set the tilt angle of the compression plate to a second value greater than the first value when the angle of the placement surface with respect to the horizontal plane makes a second angle larger than the first angle,
set the tilt angle of the compression plate such that, when the placement surface of the breast placement stage on which the breast is placed is tilted with respect to the horizontal plane, the angle made by the compression plate and the breast placement stage at the time of pressing the breast becomes greater as the angle of the placement surface with respect to the horizontal plane becomes greater; and
set, when the angle of the placement surface with respect to the horizontal plane is the first angle, a target value of the tilt angle of the compression plate to the first value, and set, when the angle of the placement surface with respect to the horizontal plane is the second angle being greater than the first angle, the target value of the tilt angle of the compression plate to the second value.

2. The mammography apparatus according to claim 1, wherein the processing circuitry is further configured to control driving of the compression plate in such a manner that the breast is compressed in a state where the tilt angle of the compression plate is greater than the tilt angle of the breast placement stage, and a distance between the compression plate and the breast placement stage is shorter in a lower portion of the compression plate than in an upper portion.

3. The mammography apparatus according to claim 1, further comprising:
a pressure sensor that detects a pressure applied on the breast;
wherein the processing circuitry is further configured to control driving of the compression plate so that the tilt angle of the compression plate coincides with the tilt angle of the breast placement stage when the pressure detected by the pressure sensor indicates a predetermine value.

4. A mammography apparatus, comprising:
a breast placement stage comprising a placement surface on which a breast is placed;
a compression plate that compresses the breast placed on the breast placement stage;
a compression plate moving mechanism configured to move the compression plate;
a supporting arm that supports the breast placement stage in such a manner that the stage can be tilted; and
processing circuitry configured to:
control driving of the compression plate in such a manner that the breast placed on the breast placement stage tilted by the supporting arm is supported from below and compressed,
determine a target value of a tilt angle of the compression plate in accordance with an angle of the placement surface with respect to a horizontal plane,
calculate a distance between the compression plate and the breast placement stage based on a driving state of the compression plate moving mechanism and a driving state of the breast placement stage, and
cause, when the calculated distance is greater than a predetermined value, the compression plate to move toward the breast placement stage in a state where the tilt angle is the target value, and when the calculated distance is equal to or less than the predetermined value, cause the compression plate to move toward the breast placement stage in a state where the tilt angle is smaller than the target value.

5. A mammography apparatus, comprising:
a breast placement stage comprising a placement surface on which a breast is placed;
a compression plate that compresses the breast placed on the breast placement stage;
a pressure sensor configured to detect a pressure acting on the compression plate or the placement surface, a supporting arm that supports the breast placement stage in such a manner that the stage can be tilted; and processing circuitry configured to:
- control driving of the compression plate in such a manner that the breast placed on the breast placement stage tilted by the supporting arm is supported from below and compressed,
- determine a target value of a tilt angle of the compression plate in accordance with an angle of the placement surface with respect to a horizontal plane, and
- cause, when the pressure detected by the pressure sensor is greater than a predetermined value, the compression plate to move toward the breast placement stage and gradually increase the tilt angle and then gradually decrease the tilt angle.

* * * * *